A
United States Patent [19]
Puhler et al.

[11] Patent Number: 4,680,264
[45] Date of Patent: Jul. 14, 1987

[54] CLASS II MOBILIZABLE GRAM-NEGATIVE PLASMID

[75] Inventors: Alfred Puhler; Reinhard Simon; Ursula Priefer, all of Bielefeld, Fed. Rep. of Germany

[73] Assignee: Lubrizol Genetics, Inc., Boulder, Colo.

[21] Appl. No.: 510,334

[22] Filed: Jul. 1, 1983

[51] Int. Cl.$^4$ .................. C12N 15/00; C12N 1/20; C12N 1/00; C07N 17/00
[52] U.S. Cl. ..................... 435/172.3; 435/253; 435/317; 935/26; 935/29; 935/23; 935/72; 536/27
[58] Field of Search ............ 435/172.3, 253, 317; 935/22, 23, 26, 27, 29, 66, 72; 536/27

[56] References Cited
PUBLICATIONS

Simon et al, *Molecular Genetics of the Bacteria-Plant Interaction*, (A. Puhler, ed.) pp. 98–106, 1983.
Change et al, *J. Bact.*, vol. 134, pp. 1141–1156, 1978.
*8th North American Rhizobium Conference Abstract Book*, pp. 1–3, 7–15, 20, 22, 25, 28–29, 42–43, 100–103, 105, 128, 130, 132 and 136 (Aug. 3–7, 1981).
*Proceedings, 8th North American Rhizobium Conference*, pp. 90–114, (K. W. Clark & J. H. G. Stephens, eds., 1983).
Bagdasarian, M. et al., (1979) in "Plasmids of Medical, Environmental, and Commercial Importance" (K. N. Timmis and A. Puhler, eds.) Elsevier, Neth., Holland.
Bagdasarian, M. et al., (1981) Gene 16: 237–242.
Bagdasarian, M. et al., (1982) Microbial Drug Resistance, Proc. 3rd Int'l. Symp., Tokyo, (S. Mitshuhashi, ed.) p. 183.
Ditta, G. et al., (1980) Proc. Nat. Acad. Sci., U.S.A., 77:7347.
Priefer, U. B. et al., (1980) in "Antibiotic Resistance, Transposition and Other Mechanisms" (S. Mitshuhashi, L. Rosival, V. Krcmery, eds.) Springer-Verlag, pp. 91–95.
Simon, R., (1980) in "Antibiotic Resistance, Transposition and Other Mechanisms" (S. Mitshuhashi, L. Rosival, V. Krcmery, eds.) Springer-Verlag, Berlin, pp. 35–42.
Simon, R. et al., (1983) Analysis of Plasmid Borne Genes in *Rhizobium meliloti*, by Tn5 Mutagenesis, Winnipeg Symposium, Proc. N. Amer. Rhizobium Conf., Jan. 1983, (meeting held in 1981).

*Primary Examiner*—Thomas G. Wiseman
*Assistant Examiner*—Jayme A. Huleatt
*Attorney, Agent, or Firm*—Lorance L. Greenlee

[57] ABSTRACT

Vectors capable of replication in a broad host range of gram-negative bacteria are provided. The vectors are composite plasmids comprising a segment derived from an *E. coli* vector plasmid and a segment derived from a broad host range plasmid. The broad host range plasmid segment includes Mob-functions and DNA coding for replication functions with regions non-essential for broad host range replication or mobilizablity having been deleted. Bacterial strains containing the above plasmids as well as methods of cloning DNA employing such plasmids are also provided.

27 Claims, 6 Drawing Figures

Construction of an RP4-Mobilisator-strain

Coselection on Km Tc
in recA⁻ backround

Spontaneous integration of
RP4 into the chromosome

Curing of pSR120

FIG. 1

FIG. 2

PLASMID pSUP104 = pAC184 + (REP,MOB)
o size determined by electronmicroscopic investigation is 3.17 μm (±1.9%) (9.5 kb)
o the black region is derived from pKT 210

FIG. 3

PLASMID pSUP106

FIG. 4

PLASMID pSUP204 = pBR325 + (REP,MOB)
° approximate size is 12 kb
° the black region is derived from pKT210

FIG. 5

PLASMID pSUP304 = pAC177 + (REP, MOB)
- approximate size is 9 kb
- the black region is derived from pKT 210

FIG. 6

CLASS II MOBILIZABLE GRAM-NEGATIVE PLASMID

BACKGROUND AND PRIOR ART

The field of the invention disclosed herein relates generally to vectors and plasmids that can replicate in a broad range of gram-negative host bacterial species. There have been several broad host range plasmids, described in the prior art, capable of being transmitted by bacterial conjugation and capable of replicating in a broad range of gram-negative bacteria. Furthermore, such plasmids have been modified to improve their suitability as cloning vehicles in gram-negative strains. See, e.g., Bagdasarian, M., et al., in "Plasmids of Medical Environmental and Commercial Importance" (K. N. Timmis and A. Puhler, eds.), Elsevier, Neth. Holland (1979) p. 411; Bagdasarian, M., et al., Gene 16, 237 (1981); and Bagdasarian, M., et al., in "Microbial Drug Resistance, Proc. 3rd Intl. Symp. Tokyo" (S. Mitsuhasi, Ed.) (1982) p183 and Ditta, G., et al., Proc. Nat. Acad. Sci. USA 77, 7347 (1980). Examples include RSF1010, a natural isolate, which belongs to incompatibility group Q and is mobilizable by plasmids of incompatibility groups P or Q, but not self-transmissable. (For a general discussion of incompatibility groups, see Datta, N. "Plasmids of Medical, Environmental and Commercial Importance", ibid. page 3.) The behavior of such vectors stands in sharp contrast with the plasmids commonly used for genetic engineering in *E. coli*. Such plasmids display a very narrow host range within which they are able to replicate, despite the fact that *E. coli* is itself a gram-negative organism. In the case of the commonly used *E. coli* vectors, their replication is confined to *E. coli* and closely related species, such as Salmonella. Their usefulness is therefore confined to genetic manipulations in *E. coli* and its close relatives (hereinafter referred to as the *E. coli* group). Genetic enginnering and recombinant DNA work outside the *E. coli* group has heretofore been severely limited by the availability of plasmids having useful features, such as drug-resistance markers, a variety of well-placed insertion sites, and the like. Modifications of the natural broad host range plasmid RSF1010 have provided some improvements, such as the plasmid pKT210, see Bagdasarian, M. et al., in "Plasmids of Medical, Environmental and Commercial Importance", supra page 411. Plasmid pKT210 has two drug-resistance genes, for chloramphenicol and for streptomycin together with two potential insertion sites, HindIII and EcoRI. The general usefulness of pKT210 is limited somewhat by the nature of the drug-resistance markers. For example, the chloramphenicol resistance gene is poorly expressed in *Rhizobium meliloti* and further, one of the more commonly used strains of *R. meliloti*, strain 2011, already carries a streptomycin resistance marker. Plasmids RSF1010 and pKT210 cannot be used for cosmid cloning since they lack a cos site. A difficulty encountered with prior art vectors that contain a cos site has been plasmid instability when the plasmid is used to carry large inserts in the range of 30-40kbp such as normally used for cosmid cloning.

It would therefore be highly advantageous to obtain an improved cloning vector, that has retained the broad host range of plasmids such as RSF1010 and pKT210 while carrying improved genetic markers and a wider variety of useful insertion sites. Further, it would be highly desirable to obtain such a plasmid in a form that is stable when bearing a large DNA insert, such as are employed in cosmid cloning. Still further, such a vector should be capable of high copy number replication in host cells.

SUMMARY OF THE INVENTION

The present invention provides improved vectors capable of replication in a broad host range of gram-negative bacterial strains. The improvements include, removal of regions non-essential for broad host range replication or mobilizability, addition of a segment derived from an *E. coli* vector providing useful insertion sites and genes for selection, and selection for stable replication in a rec+ host when bearing a large insert (up to 40kbp).

The invention combines the advantages of conventional genetic engineering vectors commonly used in *E. coli* and capable of replicating in *E. coli* with the capability of replicating and being mobilizable in a broad range of gram-negative bacterial strains. Plasmids with such attributes are constructed, according to the invention, by recombining segments of an *E. coli* vector and a broad host range plasmid. The segment of the broad host range plasmid is preferably the smallest that includes Mob-functions and DNA coding for all replication functions in at least the host range of the plasmid from which it was derived. The Mob-functions are those necessary for mobilization of the plasmid to enable its transfer by bacterial conjugation. Mobilization of RSF1010 and derivations thereof requires the activity of certain Mob genes, which act in trans, a Mob-site, believed to include the transfer replication origin, termed nic or oriT by different authors, and a set of tra functions, also acting in trans. The portion of the plasmid that includes the Mob functions and Mob-site is designated the Mob-locus, herein. The tra functions of plasmid RP4 have been found to be capable of rendering transmissible plasmids carrying only the Mob-locus of RSF1010 or its derivations. The broad host range segment contains a Mob-site but does not include tra genes. Therefore the results composite plasmid is mobilizable but not self-transmissable. Transfer to a recipient host by bacterial conjugation can occur whenever the tra functions are present in the donor host cell, either on the chromosome or on another plasmid.

The term "*E. coli* vector plasmid" includes generally any of the autonomously replicating plasmids recognized by those of ordinary skill as useful in genetic engineering, cloning, gene mapping and gene transfer, and gene expression in connection with *E. coli* or members of the *E. coli* group, comprising a replicon whose functional range is limited to the *E. coli* group. Examples of *E. coli* vector plasmids include, but are not limited to, pMB9, pBR322, pBR325, pKB111, pUC-8, pUC-9, pACYC184, pACYC177, pSC101, and the like.

The DNA segment derived from an *E. coli* vector plasmid includes at least a segment coding for antibiotic resistance and a restriction site unique to both the *E. coli* vector segment and the broad host range segment. Preferably a larger portion is included and the entire vector may be incorporated into the composite. Incorporating most or all of the *E. coli* vector plasmid provides an increased number of unique restriction sites at useful loci, and a variety of selection markers, such as antibiotic resistance genes.

The disclosed composite plasmids can be further modified so that they remain stable in a host cell, even when carrying large inserts of about 30–40kbp, such as are employed, e.g. in cosmid cloning. Such modifications include the addition of a cos site and an additional selection for stability in a recombination-proficient (RecA+) host. A composite plasmid is described herein that combines, in addition to broad host-range replication, mobilizability and an *E. coli* vector plasmid segment, the ability to replicate stably in a gram-negative host while carrying a large insert.

Composite plasmids of the type generally described are termed Class II vectors herein. The Class II vectors are useful in the genetic modification of a broad range of gram-negative bacterial strains. Examples of gram-negative bacteria include, but are not limited to, members of the genus Klebsiella, Rhizobia, Agrobacteria, Psdeudomonas, and Azotobacter, in addition to the *E. coli* group. Among the gram-negative bacteria are strains capable of carrying out a complex variety of reactions, many of which are industrially useful. For example, the conversion of atmospheric nitrogen to ammonia, the hydrolysis of cellulose to glucose and the degradation of toxic waste substances are among the known capabilities of certain gram-negative species. In addition, many species are capable of growth and/or survival under extreme environmental conditions that destroy or inactivate most strains, including conditions of pH, temperature, salinity and the like, which are encountered in some industrial processes. Class II vectors can be used to transfer genetic information coding for a useful function from any source to a gram-negative host, thereby enhancing the useful properties of the host by the additional function. For example, the genes of *Pseudomonas cellulosa* coding for the known cellulose-hydrolyzing enzymes of this organism when cloned into a composite vector of the present invention and transferred into a strain of Azotobacter, a free-living, nitrogen-fixing strain, result in a modified organism capable of efficiently converting cellulosic biomass to high quality organic fertilizer. In addition, the stable Class II vectors disclosed herein are useful as cosmid vectors for genetic material derived from gram-negative bacteria.

DETAILED DESCRIPTION OF THE INVENTION

That portion of a Class II vector derived from an *E. coli* vector plasmid can, in principle, be derived from any desired *E. coli* vector plasmid, chosen on the basis of its known utility, its cloning sites and the convenience of its selection markers, all according to criteria of significance in context of the intended use, as will be understood by those of ordinary skill in the art. Examples of suitable *E. coli* vector plasmids include, but are not limited to, pACYC184, pBR325 and pACYC177.

The choice of a suitable broad host range, mobilizable replicon is based primarily upon the range of its transmissibility and ability to replicate. Other factors, such as its incompatibility group, may influence the choice of replicon in specific instances. In general, however, plasmids having the broadest range of potential host bacteria are preferred. The principles of construction and the teachings herein can also be applied to construct Class II vectors that replicate in those gram-negative strains where generally broad host range plasmids fail to replicate. The disclosed principles of Class II vector construction therefore apply to the construction of a family of such vectors able to replicate and mobilize in any gram-negative organism, even though there might exist individual strains in which one or more such vectors would be unable to replicate.

The Class II vectors described in the Examples 2–4 were based upon the broad host range plasmid RSF1010 or its derivative, pKT210. Preferably, the length of the DNA segment obtained from a broad host range plasmid will be held to a practical minimum so that the size of the resulting composite plasmid will be minimized. There is generally believed to be an inverse relationship between the size of the plasmid and its stability. (The terms "composite plasmid" and "Class II vector" are used interchangeably herein.) The desired segment to be incorporated into the composite need not be bracketed by unique restriction sites or even mapped in detail. If there exist restriction sites that occur relatively frequently throughout the broad host range plasmid, partial digestion with the appropriate restriction endonuclease will yield a distribution of fragment sizes representing all regions of the plasmid. The restriction endonuclease Sau3A is often useful for such partial digestions. Sau3A recognition sites are found with a relatively high frequency and random distribution in most plasmids. Other restriction enzymes could be used in a similar manner in many instances, and the choice of an appropriate enzyme for a given vector would be apparent to one of ordinary skill in the art based upon a published restriction map or upon restriction site data obtainable by one of ordinary skill in the art without undue experimentation.

The construction of specific Class II vectors, their selection and use in specific instances are described in detail in the following examples. The abbreviations used in the examples and elsewhere in the specification are those commonly accepted for publication in standard journals such as those cited herein. When not otherwise specified, reagents and materials described herein are obtainable from commercial sources. Unless otherwise specified, restriction enzymes, DNA ligase and other enzymes were used under conditions specified by the manufacturer or as set forth in the referenced published procedures. Where not otherwise specified, standard procedures, such as those set forth in *Methods in Enzymology* Vol. 68, R. Wu, Ed. (Academic Press, New York 1979) were employed.

EXAMPLE 1

Construction of a Mobilizing Strain

Two derivatives of plasmid RP4 were forced by the choice of selection conditions to coexist in a recA− *E. coli* host. RP4-2-Tc::Mu was derived from RP4-2 by insertion of phage Mu into the tetracycline resistance gene of RP4-2. (See U. B. Priefer, et al., in *Antibiotic Resistance, Transposition and Other Mechanisms*, (S. Mitshuhashi, L. Rosival and V. Krcmery, Eds.) Springer Verlag, Berlin (1980), page 91; and R. Simon, ibid., page 35, for description of RP4-2 and the general methodology of Mu insertion.) Plasmid RP4-2-Tc::Mu is ampicillin-sensitive ($Ap^s$), tetracycline-sensitive ($Tc^s$), kanamycin-resistant ($Km^r$) and $tra^+$. The plasmid was introduced into a recA− strain of *E. coli* by conventional conjugation. The recA− strains used in this study were CSH52, (Miller, J. H., *Experiments in Molecular Genetics*, Cold Spring Harbor Laboratory (1972); C600(recA), (Appleyard, R. K., Genetics 39, 440 (1954); parent strain: ATCC #23724; and *E. coli*294-(recA), (Cold Spring Harbor Laboratory, New York; parent strain: ATCC #31446). Both C600 and 294 were made recA− by contransduction of a known RecA− deletion mutant with a closely linked selectable marker identified by Tn10 insertion, using phabe P1 as the transducing agent. Approximately 50% of Tc$^r$ transductants were RecA−.

The second RP4 derivative employed was pSR120, a fusion product of plasmids pSR100 and ColE1. pSR100 is a "mini RP4", described by Simon et al., supra, isolated as a deletion of RP4 lacking kanamycin resistance and tra functions. pSR120 was derived from pSR100 and ColE1 by joining the two at their unique EcoR1 sites, after digestion with EcoR1 endonuclease and rejoining with DNA ligase. pSR120 was Ap$^r$ and Tc$^r$.

The plasmid pSR120 was introduced into a recA− strain of E. coli containing the plasmid RP4-2-Tc::Mu by transduction with phage P1. The cells were plated on medium containing 25 mg/l kanamycin and 5 mg/l tetracycline. The initial selection yielded several hundred colonies which were very small, indicating poor growth. However, after prolonged incubation, up to three days, a few normal-sized colonies were observed. Cultures derived from these normally-growing colonies were further characterized by gel electrophoretic analysis of plasmid DNA and ability to transfer chromosomal genes. In this manner it was possible to identify strains which retain the Km$^r$ and tra+ phenotype but which lacked RP4-2-Tc::Mu, indicating that the latter plasmid was integrated in the chromosome.

The plasmid pSR120 was cured from strains containing RP4-2-Tc::Mu integrated in the chromosome. The strain to be cured was grown for about 40 generations in LB medium (Luria broth) (Miller, J., *Experiments in Microbial Genetics*, Cold Spring Harbor Laboratory, New York), containing 100 mg/l acridine orange (AO). After the AO treatment, the culture was enriched for Tc$^s$ cells by incubation in the presence of 5 mg/l tetracycline and 10 mg/l cycloserine. Growth in the presence of tetracycline was lethal to Tc$^r$ cells in the presence of cycloserine. The cycloserine enrichment procedure was repeated twice. Gel electrophoretic analysis of plasmid DNA isolated from Tc$^s$ clones showed that pSR120 was lost. Three clones have been isolated and characterized as described, and their characteristics are shown in the following table:

| strain number | integrated plasmid | resistance markers RP4 | chrom. | other important properties |
|---|---|---|---|---|
| S 68-7 | RP4-2(Tc::Mu) | Km | Sm | Thi, Pro, His, su− |
| SM 10 | " | Km | — | Thi, Thr, Leu, su$_{III}$ |
| S 17-1 | RP4-2(Tc::Mu)(Km::Tn$^7$) | Tp-Sm | — | Pro, res− mod+ |

Figure 1:
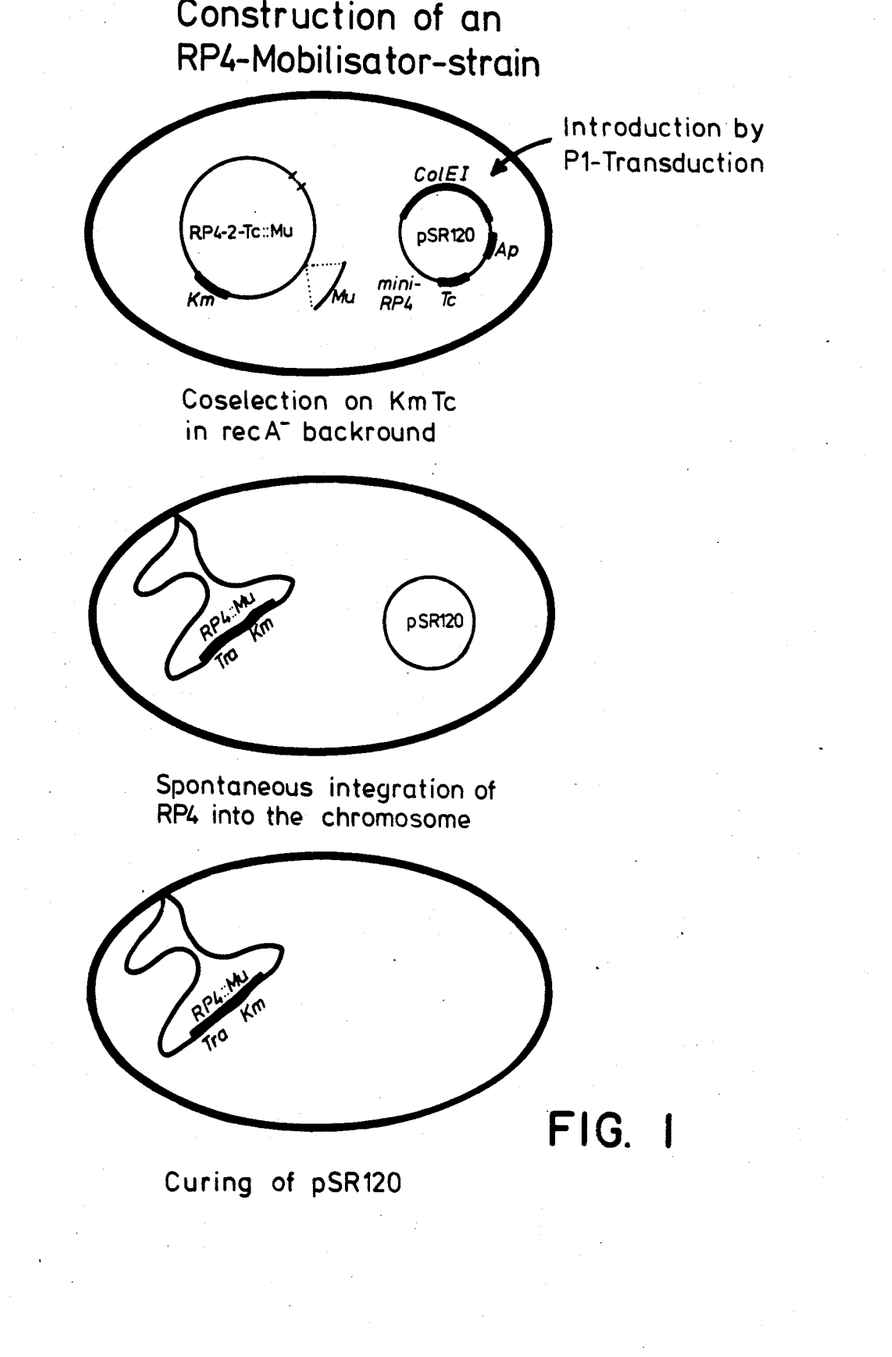

Strain S68-7 was obtained using E. coli CSH52 as the recA− host, strain SM10 was obtained using E. coli C600 and S17-1 was obtained from E. coli 294. In addition, in strain S17-1, the Km$^r$ was abolished by a Tn7 insertion. Strain S17-1 carries resistance to trimethoprim (Tp) and streptomycin (Sm), and is restriction-deficient. A schematic respresentation of the construction of a mobilizing strain as described herein, is shown in FIG. 1.

EXAMPLE 2

Class II Vector Construction

The following constructions were based on the strategy of inserting random fragments of a broad host range plasmid such as pKT210, a Cm$^r$ derivative of the broad host range plasmid RSF1010, described by Bagdasarian et al. in *Plasmids of Medical, Environmental and Commercial Importance, supra,* into an E. coli vector plasmid such as pACYC184, pACYC177, or pBR325 linearized by a single cut with Sau3A or BamHI. The recombinants were selected for drug resistance carried by the E. coli plasmid, mobilizability and ability to replicate in a gram-negative organism outside the E. coli group. Plasmid RSF1010 and its derivatives including pKT210 are mobilizable by plasmid RP4 so that the mobilizing strains described in Example 1 could be used for conjugal transfer for the resulting hybrid plasmids.

Two types of partial Sau3A digestion were employed. One was designed to yield randomly cut segments of pKT210 containing the Mob-locus and all necessary functions for broad host range replication. The other was designed to produce single cuts at random in one of the chosen E. coli vectors to produce linear plasmid DNA of full contour length. To establish optimal conditions for a partial digestion of pKT210, a constant amount of DNA was treated with a dilution series of Sau3A endonuclease ranging from undiluted to 1:200 dilution (by volume) for a defined period of time (e.g., 15 minutes) under reactions conditions of buffer and incubation temperature as recommended by the manufacturer. Treated DNA was tested to determine the degree of digestion by electrophoresis on agarose gel, comparing uncut and completely digested DNA along with conventional size standards. Large scale digestion was then carried out, using 10 μg of pKT210 DNA and the amount of Sau3A endonuclease which produced the maximum number of fragments in the range from 4 to 8kb.

The E. coli vectors pACYC184 and pBR325 were linearized with a single random Sau3A cut in order to conserve a BamHI site as well as the Tc$^r$ marker gene carried on those plasmids. Digestions with a dilution series of Sau3A, as described supra, were again carried out; however, in this instance the criterion was to determine the enzyme concentration which produced the largest proportion of linear, full-sized plasmid DNA molecules in relation to uncut DNA and smaller digestion products. Using the chosen enzyme concentration, a large scale digestion was carried out on about 10 μg of plasmid DNA. To enrich the proportion of linear full-length molecules, the digest was loaded on a sucrose gradient from 5% (w/v) to 20% (w/v) sucrose and centrifuged in a swinging bucket rotor for 4 hours at 35,000 rpm, in an SW-40 rotor, Beckman Instrument Company, Fullerton, Calif. Fractions were collected and analyzed by agarose gel electrophoresis. Those fractions containing linear molecules were pooled, dialyzed against TE buffer (10 mM Tris, 1 mM EDTA, pH 7.5) and the DNA therein was recovered by conventional steps of phenol extraction and ethanol precipitation.

In the case of plasmid pACYC177, the vector DNA was treated by complete digestion with BamHI endonuclease. The single BamHI site in pACYC177 maps outside of any drug resistance gene. Since cleavage by Sau3A and BamHI leaves the same sequence of unpaired bases at the cut ends, Sau3A and BamHI-cut ends are readily annealed and ligated to one another. The joining of a Sau3A fragment of pKT210 to BamHI cut pACYC177 results in loss of the BamHI site in most instances; however, such loss was considered acceptable for purposes of the described constructions.

In all cases, the linearized vector DNA was pretreated with alkaline phosphatase in order to prevent religation of the vector DNA.

Ligation was carried out under standard incubation conditions using the enzyme DNA ligase and an excess of pKT210-Sau3A fragments over linear vector DNA.

The ligation mixture was used to transform one of the mobilizing strains described in Example 1. Transformants were selected for ability to form colonies in the presence of an antibiotic for which resistance was conveyed by a gene on the E. coli vector.

The transformants were first selected for mobilizability. Transformants were transferred onto a plate containing selective media containing antibiotic, and colonies were replica plated onto a lawn of an E. coli recipient strain spread on a rich medium, which constituted the mating plate. The mating was allowed to take place for several hours at 37° C. and the mating plate was then replica plated onto a selective medium containing two antibiotics, one selective for recipient and the other selective for the presence of the vector. Colonies of transconjugants obtained in this manner were thereby selected to have received a mobilizable hybrid plasmid.

Those transformants which proved to contain a mobilizable vector plasmid were then mated with R. meliloti2011 Sm$^r$ either by replica mating, as described supra, or by single crosses on nitrocellulose filters. Transconjugants arising from such matings must have acquired a Mob+ hybrid vector plasmid with additional broad host range replication capability. Transformants obtained in the original selection for a Mob+ plasmid were pooled and mixtures containing 100 to 300 colonies were directly mated with R. meliloti2011 Sm$^r$. For replica matings, the mixed donor colonies were transferred onto selective medium and replica plated on a 2011 lawn spread on rich medium. This mating plate was incubated for several hours at 30° C. and subsequently replica plated onto selective medium. For filter matings, the mixed donor colonies were first suspended in liquid medium and mixed with a culture of R. meliloti2011. Aliquots of this mating mixture were incubated on nitrocellulose filters for several hours at 30° C. The conjugation mix was subsequently resuspended in buffer and plated onto selective medium containing Sm and one of the E. coli vector specific antibiotics. All R. meliloti transconjugants arising from this selection procedure must necessarily have obtained a plasmid carrying both the mobilization and replication functions of pKT210 (Mob+/rep+).

Plasmids obtained from Mob+/rep+ R. meliloti were further analyzed to determine whether other markers derived from the E. coli plasmid were present in the hybrid, for stability of replication in R. meliloti and for molecular size. Plasmids with the desired properties were re-isolated from R. meliloti, re-introduced into E. coli by transformation and further characterized to determine mobilization frequency, restriction map and host range.

Care must be taken to insure that the E. coli strain to be transformed with DNA extracted from R. meliloti is one which is restriction deficient, that is, one which fails to degrade plasmid DNA which has previously replicated in R. meliloti. The mobilizing strain S17-1 is restriction deficient and may be directly transformed with plasmid DNA isolated from R. meliloti. However, the mobilizing strain SM10 is not restriction deficient and plasmids isolated from R. meliloti must first be passed through a restriction deficient E. coli strain such as 294.

Figure 2:
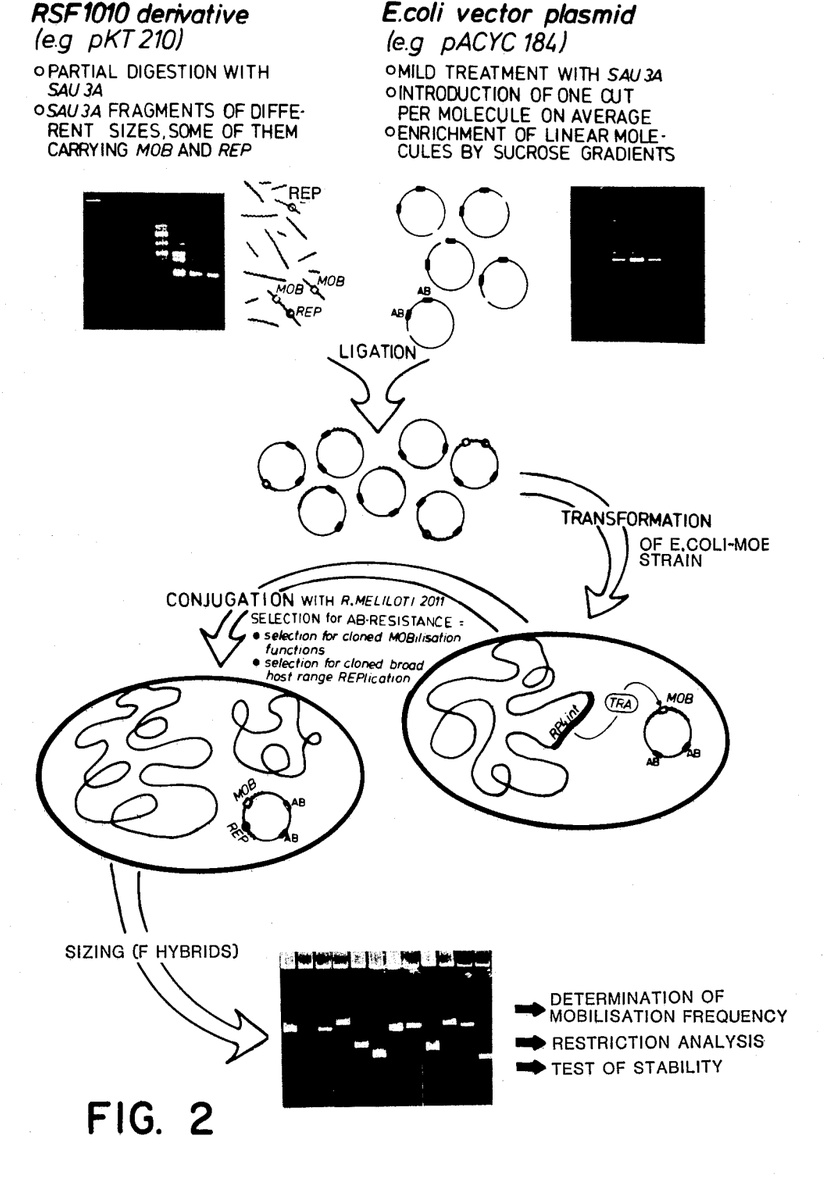

The general scheme of Class II vector construction is shown diagrammatically in FIG. 2.

Construction of pSUP104

Plasmid pACYC184 (about 10μg in 500 μl) was bated with 5 μl of Sau3A endonuclease diluted 1:6 (by volume) for 10 minutes at 37° C., using a standard buffer recommended by the manufacturer.

Plasmid pACYC184 (about 10 82 g in 500 μl) was digested with 30 μl of Sau3A endonuclease diluted 1:100 (by volume) for 15 minutes at 37° C. Linear plasmid DNA was separated from smaller fragments and uncut circles by sucrose gradient centrifugation as described, supra. After dialysis, the linear DNA was treated with alkaline phosphatase, extracted with phenol and recovered by ethanol precipitation. The purified DNA was resuspended in 50 μl of TE buffer to a final concentration of about 20 μg/ml.

For the ligation reaction, about 0.5 μg of pACYC184 DNA (partial Sau3A digest) and about 1 μg of pKT210 linear DNA were mixed in a standard DNA ligase reaction mixture in the presence of DNA ligase. The ligation reaction was carried out under standard conditions. Aliquots of ligation mix were used to transform the mobilizing strain SM10 (Example 1) and transformants were selected for Tc$^r$ derived from the pACYC184 portion of the recombinant plasmid. Note that selection for Cm$^r$ was not possible since this would also select for the transformation of undigested pKT210 molecules.

Some of the SM10 transformants, selected as described, were used for a replica mating with an E. coli recipient strain, E. coli S51.12 Sm$^r$, again selecting for Tc$^r$ transconjugants. Out of 1300 replica plated colonies, 91 showed transfer of the Tc resistance marker, indicating that these plasmids were also Mob+. The 91 SM10 colonies known to be Mob+ were subsequently mated with R. meliloti2011 Sm$^r$ by replica mating. Eleven Tc$^r$ R. meliloti transconjugants were recovered. Therefore, out of 1300 tested SM10 colonies, 11 contained hybrid molecules having both the Rep and Mob functions of pKT210.

The remainder of the SM10 transformants initially obtained from the ligation mixture were scraped together and the mixtures were directly replica mated with R. meliloti2011 Sm$^r$, as described, supra. More than 100 Tc$^r$ R. meliloti transconjugants were identified on plates containing Tc and Sm. A total of 117 Tc$^r$ R. meliloti transconjugants were tested for Cm resistance, which proved to be present in 66 of the 117 strains. The plasmids sizes were estimated by gel electrophoresis and 20 plasmids in the size range from about 9 kb to 10 kb were isolated and retransformed into E. coli where they were further characterized for mobilization frequency, stability and restriction map.

Figure 3:
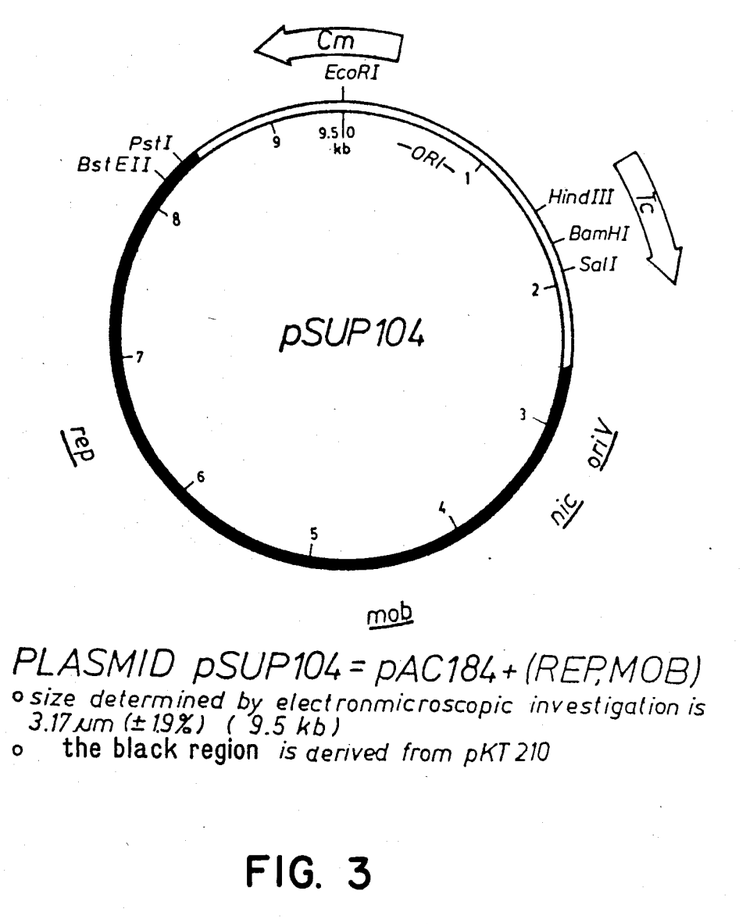

Most of the plasmids were easily mobilized into R. meliloti; some, however, were not stably maintained in this host. All stable derivatives were found to contain a pKT210 fragment of about 6 kb and this fragment carried recognition sites for PstI and BstEII near one end. Plasmid pSUP104 was selected from the group of stable derivatives and a partial restriction and genetic map is shown in FIG. 3.

Construction of pSUP106

Figure 4:
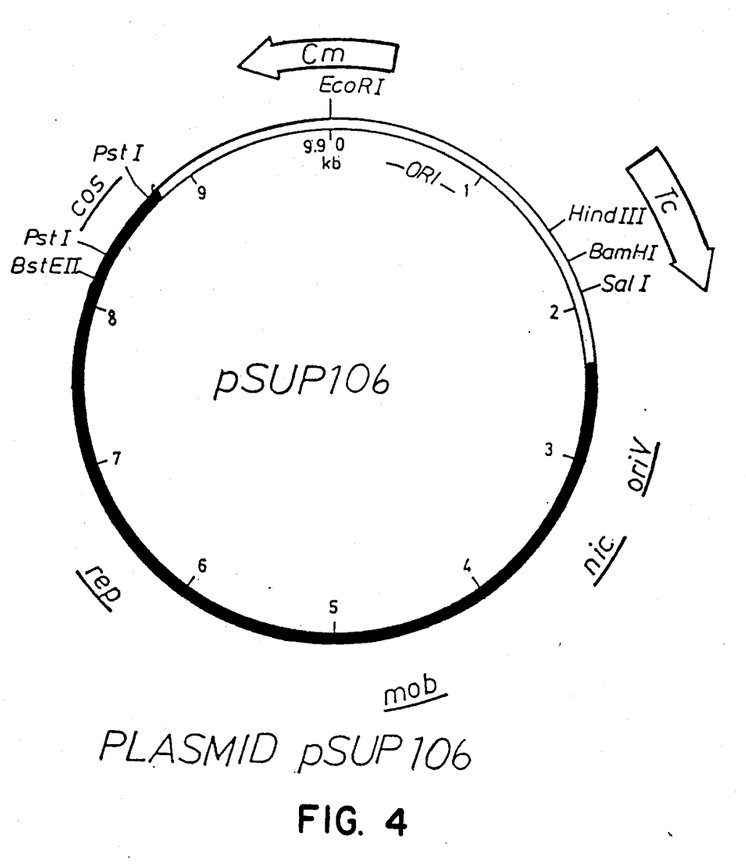

Plasmid pSUP106 is a cosmid-cloning vector derived from pSUP104 by insertion of a 400 bp PstI fragment containing a cos site derived from plasmid MUA10. For this purpose, the single PstI site derived from the inserted pKT210 fragment was employed. A partial genetic and restriction map of pSUP106 is shown in FIG. 4. Plasmids pSUP104 and pSUP106 are characterized as derived from the *E. coli* vector pACYC184, carrying Mob and Rep functions of plasmid pKT210. Both hybrid plasmids carry genes for resistance against Cm and Tc. They bear unique recognition sites for EcoRI (within Cm), ClaI, HindIII, BamHI and SalI, all within Tc. Plasmid pSUP106 is further characterized by containing a cos site and is suited for cosmid cloning experiments.

Construction of pSUP204

A portion of the partial Sau3A digest of pKT210, described supra for the construction of pSUP104 was used as the source of DNA fragments of pKT210.

Plasmid pBR325 (approximately 10 μg) was digested with 5 μl of Sau3A endonuclease diluted 1:10 (by volume) for 15 minutes at 37° C. under standard reaction conditions for Sau3A endonuclease. The digested DNA was also treated with alkaline phosphatase and linear full length plasmid DNA molecules were then purified by sucrose gradient centrifugation as described supra.

The ligation reaction was carried out under standard conditions in the presence of DNA ligase, the reaction mixture containing about 1 μg of linear pBR325 DNA and about 3 μg of pKT210 DNA (partial Sau3A digest). After completion of the reaction, aliquots of the ligation mix were used to transform SM10 (Example 1) and transformants were selected for ability to grow on plates containing ampicillin, using the Ap resistance gene derived from pBR325.

Some 300 to 500 of the resulting Ap$^r$ transformant colonies were scraped together and incubated in liquid medium containing Cm. The donor cultures of cells that had grown up in liquid medium were conjugated with *R. meliloti*2011 Sm$^r$ on nitrocellulose filters using the filter mating technique described supra. Transconjugants were selected by growth on plates containing Sm and Tc. Of 20 different donor cultures obtained in the manner described, 9 gave rise to Tc$^r$ *R. meliloti* transconjugants. All such transconjugants carried the Rep and Mob functions of pKT210 and the Tc$^r$ gene of pBR325.

The Tc$^r$ *R. meliloti* transconjugants were further tested for Cm and Ap resistance. Colonies that were Ap$^r$, Cm$^r$, Tc$^r$ were further tested to determine the sizes of their hybrid plasmids using gel electrophoresis. The smaller plasmids were isolated and retransformed into *E. coli* for further analysis.

Figure 5:
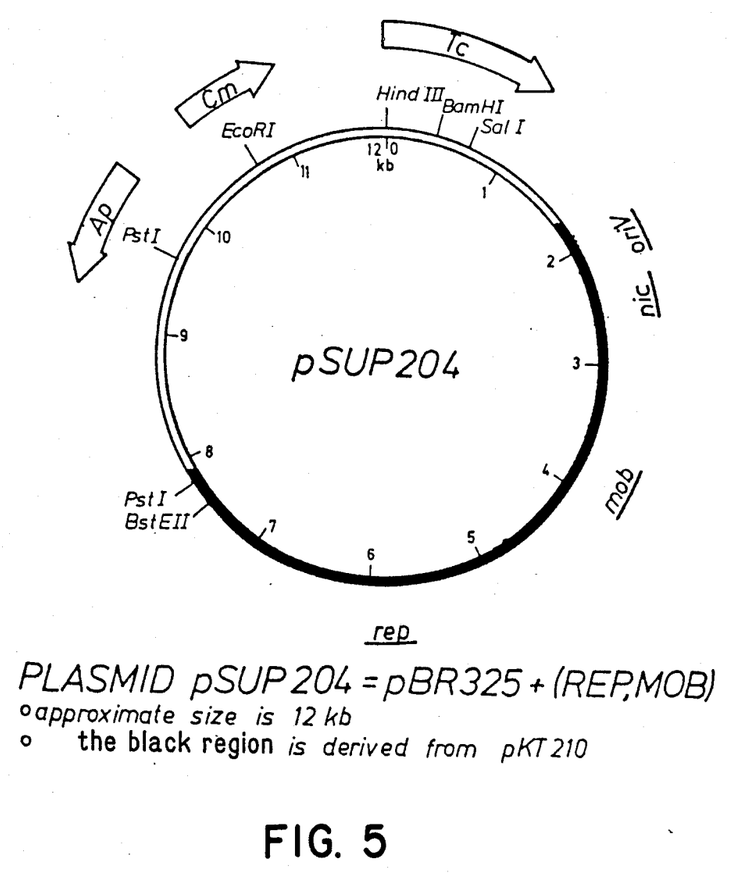

A partial genetic and restriction map of pSUP204 is shown in FIG. 5. The hybrid plasmid carries a pKT210 fragment of about 6 kb with recognition sites for PstI and BstEII. The plasmid is efficiently mobilized; however, it tends to be rapidly lost in Rhizobium grown under nonselective conditions.

Construction of pSUP304

The plasmid pSUP304 is a derivative of the *E. coli* vector plasmid pACYC177 which encodes resistance against Ap and kanamycin (Km) (the same gene also confers resistance to neomycin, Nm). The single BamHI site of pACYC177 maps outside of any of the known resistance genes. The site was used for cleaving the molecule to provide full length linear fragments thereof. The Rep and Mob functions were in this instance derived from plasmid pSUP104, described supra.

Plasmid pSUP104 DNA (about 8 μg) was digested with 20 μl of Sau3A endonuclease diluted 1:60 (by volume) for 15 minutes at 37° C., using the standard reaction buffer for Sau3A digestion. Aliquots of the digest were used for subsequent ligation with linear, BamHI-treated pACYC177.

Plasmid pACYC177 (approximately 10 μg) was completely digested with BamHI endonuclease, using the standard buffer reaction conditions for complete BamHI digestion. The single-cut plasmid DNA was further treated by digestion with alkaline phosphatase. The digests were phenol extracted and the DNA was ethanol-precipitated.

About 0.5 μg of pACYC177 linear DNA was mixed with about 2 μg of pSUP104 DNA (partial Sau3A digest) with DNA ligase in a standard ligase reaction mixture, incubated under standard ligase reaction conditions. Aliquots of the ligation mixture were used to transform SM10 (Experiment 1) and transformants were selected for growth on medium containing ampicillin, indicating acquisition of the Ap resistance derived from pACYC177.

A total of 500 Ap$^r$ SM10 transformants were replica mated with a Sm$^r$ *E. coli* recipient (S51.12). Transconjugants were selected for Km resistance. Of the 500 donor colonies, 24 yielded Mob+ vector plasmids. Each of the 24 SM10 colonies was grown in liquid culture to log phase and separately conjugated with *R. meliloti*2011 Sm$^r$ on nitrocellulose filters, as described supra. *R. meliloti* transconjugants were selected for neomycin resistance. Of the 24 donor strains, 10 gave rise to Nm$^r$ transconjugants which had both the Rep and Mob functions derived from pSUP104.

Transformants containing Rep+ Mob+ hybrid plasmids were also directly selected by scraping together 100 to 200 SM10 transformants of the initial ligation mix and growing the mixture in liquid culture. The mixed donor culture was then separately mated with *R. meliloti*2011 Sm$^r$ on nitrocellulose filters as described, supra, selecting for transconjugants capable of growth on medium containing Nm and Sm. Plasmid DNA from colonies of Nm$^r$ *R. meliloti* transconjugants was further characterized in terms of size, mobilization frequency and stability as described, supra.

Figure 6:
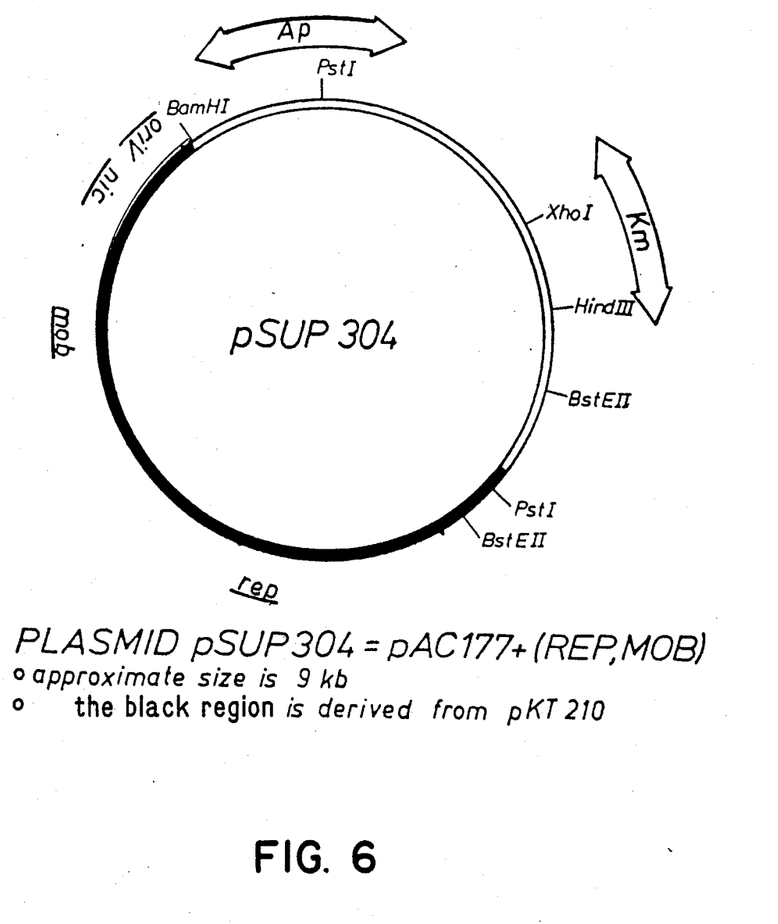

The resulting plasmid, chosen as representing the most favorable combination of characteristics was designated pSUP304 and a partial genetic and restriction map thereof is shown in FIG. 6. The plasmid pSUP304 was efficiently mobilized and was stably maintained in Rhizobium in the absence of selection pressure. The inserted fragment encoding the Rep and Mob functions was about 6 kb in size and carried restriction sites for PstI and BstEII. Unexpectedly, it was found that pSUP304 contained a single BamHI site which was presumably generated in the course of the cloning procedure although its existence was not predicted. (Several BamHI-resistant plasmids were isolated from the same set of transconjugants.

The described plasmids have been tested for transfer to and stable replication in a variety of gram-negative hosts including *Rhizobium meliloti, Rhizobium leguminosarum, Rhizobium trifolii, Agrobacterium tumefaciens, Pseudomonas aeruginosa, Pseudomonas stutzerei* and Rhodopseudomonas.

Vector stability was tested by cultivating Rhizobium strains harboring one of the described plasmids in broth culture in the absence of a selection agent. After 20, 40 and 60 generations, the cultures were plated on rich medium plates and 100 colonies from each were tested for the continued presence of resistance markers carried on the respective plasmids. The presence of the resistance markers indicated continued presence of the plasmid. Table I shows the results of mobilization frequency and plasmid stability tests on each of the described vectors in two strains of Rhizobium and one strain of Agrobacterium. The copy number of each of the described plasmids in gram-negative strains has been estimated by comparing the intensity of the plasmid bands on gel electrophoresis with that obtained by plasmid pKT210 in *E. coli*. The plasmid bands in all cases are of approximately the same density, indicating, by comparison with the known copy number of pKT210 in *E. coli*, that each is present in multiple copies, on the order of about 50 per cell.

EXAMPLE 3

Isolation of Stable Cosmid Derivatives of pSUP106

When pSUP106 was used to construct a gene library of *R. meliloti* by cosmid cloning, the resulting cosmid hybrids containing inserts from about 30 kb to 40 kb provided to be stable during replication in a RecA⁻ recipient but were unstable in a RecA+ strains, the cosmid vectors had undergone deletion or rearrangements such that plasmids isolated therefrom were substantially smaller than the original vectors used to transform the RecA+ recipients. A procedure was developed which enabled selection and isolation of cosmid hybrids that remain stable in a RecA+ host while carrying an insert of 30 to 40 kb.

Total DNA of *R. meliloti* was partially digested with EcoRI endonuclease. The DNA was fractionated in a preparative gel electrophoresis at a 0.4% (w/v) low-melting agarose. That portion of the gel containing DNA in the size range from about 30 kb to 40 kb was cut from the gel and eluted in buffer after incubation at 70° C. to melt the agarose and improve the yield of DNA. The solution was extracted with phenol and DNA recovered by ethanol precipitation. The EcoRI *R. meliloti* DNA fragments were mixed with EcoRI-digested, alkaline phosphatase-treated pSUP106 in a molar ratio of about 1:3, the linear vector DNA predominating. The mixture was ethanol precipitated, re-extracted in a total volume of about 2 μl to provide a final DNA concentration of about 500 μg/ml, and incubated in a DNA ligase catalyzed reaction under standard ligase conditions. The resulting concatamers were mixed with λ phage heads in an in vitro packaging reaction, as described, e.g., by Hohn, B., in *Methods in Enzymology* 68 (R. Wu, Ed.) Academic Press (1979) p. 299, and the resulting phage were used to infect *E. coli* S17-1 (Example 1) a Rec⁻ host. Colonies of cosmid bearing cells were isolated by plating for resistance to tetracycline.

To select for stability in a RecA+ host, the cosmid hybrids were introduced, by transformation or by mating, into a RecA+ host such as *E. coli*K820, *E. coli*CSH51 or *R. meliloti*2011. The transformed cultures were grown for several generations in liquid culture in the presence of a selective antibiotic for which resistance was conferred by the plasmid. Plasmid DNA was isolated from these cells after several generations of growth and analyzed by gel electrophoresis to determine plasmid size. In the absence of further selection, it was found that stable derivations could be isolated but that these frequently had deletions leading to loss of important functions, including the cos site and the Mob-locus. In order to select for retention of the mobilizability and broad host range replication functions, the stable cosmid hybrids are transferred and retransferred between *E. coli* and *R. meliloti* hosts. If the molecules prove to be stable after several rounds of such selection, the plasmid DNA is isolated and digested with EcoRI to release the insert from the cosmid vector. The vector DNA is religated and used to transform *E. coli*. The characteristics of the vector molecule recovered from the foregoing selection procedures are analyzed. These include vector size, restriction map and any changes in phenotype associated with acquisition of the vector by host cells. Vector capable of stable replication as cosmid hybrids bearing inserts of about 30 to 40 kb in a RecA+ host are isolated following the foregoing selection process.

EXAMPLE 4

Cellulase Gene Transfer from Pseudomonas to Azotobacter

The soil-borne bacterium *Azotobacter vinelandii* is a non-symbiotic organism capable of fixing nitrogen and utilizing carbohydrates as a carbon source. Studies on the effect of Azobacter on the nitrogen content of soils have shown that the nitrogen content can be enhanced by the presence of Azotobacter when soils are inoculated with carbohydrates. However, the processes are not cost effective when comparing the cost of the carbohydrate inoculant and the yield of fixed nitrogen in the soil. Genetic manipulation to provide cellulose degrading capability in Azotobacter would make it possible to use the organism to enhance soil fertility without carbohydrate inoculation, because the modified organism would be able to degrade cellulose to provide carbohydrate. Ample supplies of cellulose are available at virtually no cost from field stubble, deciduous plant material, wheat straw and the stems and leaves of annual crops remaining after harvest.

*Pseudomonas cellulosa* DNA is extracted from a culture of the organism grown to mid-log phase and partially digested with EcoRI endonuclease. As described in Example 3, the fragments are separated by preparative gel electrophoresis in agarose and those fragments in the size range from about 30 kb to 40 kb are cut from the gel and eluted. The eluted DNA is extracted with phenol and ethanol precipitated. The *P. cellulosa* DNA fragments are mixed with EcoRI digested, alkaline phosphatase treated pSUP106 in a molar ratio of about 1:3 of *P. cellulosa* DNA to linear pSUP106 DNA. The mixture is ethanol precipitated, re-extracted in a total volume of about 2 μl to provide a final DNA concentration of about 500 μg/ml and incubated in DNA ligase catalyzed reaction under standard ligation conditions. The resulting concatamers are mixed with λ phage heads in an in vitro packaging reaction and the resulting phage are used to infect *E. coli* S17-1 (Example 1) in a RecA⁻ host. Colonies of cosmid bearing cells are isolated by plating for resistance to tetracycline. Tc$^r$ colonies are replica plated on medium containing cellulose as the sole carbon source. Those transformants able to form colonies on the cellulose medium represent those which have received a cosmid insert containing a cellulase gene of *P. cellulosa*.

Hybrid plasmids carrying a cellulase gene are re-isolated from cultures of the cellulose-containing colonies.

The inserts carrying a cellulase gene are further characterized by restriction mapping and by transposon mutagenesis to determine the relative location of the cellulase gene with respect to restriction sites within the cloned *P. cellulosa* DNA fragment. By mapping the cellulase gene with respect to restriction sites within the fragment, it is possible to isolate and identify a sub-fragment which can be inserted and stably maintained in an Azotobacter strain.

The sub-fragment, identified and isolated as described, is inserted into a cloning site, selected for convenience, in one of the Class II vectors described in Example 2. In the present Example, pSUP304 is chosen as the cloning vehicle.

Insertion of the cellulase gene fragment into pSUP304 at either the XhoI site or the HindIII site destroys kanamycin resistance conferred by the plasmid but permits selection for ampicillin resistance. Alternatively, insertion at the BamHI site permits selection with either ampicillin or kanamycin. Insertion of the cellulase DNA fragment at any of the above described sites is accomplished by conventional techniques of DNA ligation. The ligation reaction mixture is used to transform *E. coli* S17-1 (Example 1), since that strain is kanamycin sensitive. If the kanamycin resistance is not used for selection, any of the Mob strains described in Example 1 could be employed for the transformation. Transformants are initially selected for antibiotic resistance and antibiotic resistant colonies are further checked by replica plating for ability to utilize cellulose as a carbon source.

Plasmids containing an inserted cellulase gene are transferred from transformants having the correct phenotype to *Azotobacter vinelandii* by mating, followed by selection for antibiotic resistance. *A. vinelandii* transconjugants are further tested for ability to use cellulose as a carbon source and to fix nitrogen using cellulose as a carbon source. Colonies displaying the desired phenotype are used to inoculate large cultures for the purpose of extracting and characterizing the plasmid and for analysis of growth characteristics and for field tests.

The following bacterial strains, containing and replicating the indicated Class II vectors, were deposited with the U.S. Department of Agriculture, Northern Regional Research Center, 1815 North University Street, Peoria, Ill. 61604:

| Strain | NRRL Accession No. | Deposit Date |
| --- | --- | --- |
| *E. coli* CSH52/pSUP104 | B-15485 | July 1, 1983 |
| *E. coli* CSH52/pSUP106 | B-15486 | July 1, 1983 |
| *E. coli* CSH52/pSUP204 | B-15490 | July 1, 1983 |
| *E. coli* CSH52/pSUP304 | B-15493 | July 1, 1983 |
| *E. coli* SM10 | B-15481 | July 1, 1983 |
| *E. coli* S68-7 | B-15482 | July 1, 1983 |
| *E. coli* S17-1 | B-15483 | July 1, 1983. |

We claim:

1. A composite DNA plasmid capable of replication in *E. coli* that is mobilizable, not self-transmissible, and having a broad host range that is co-extensive with plasmid RSF1010, comprising:
   (a) a first DNA segment obtained from a plasmid containing a replicon functional in *E. coli;* and
   (b) a second DNA segment having a maximum length of 6 kb, said second DNA segment characterized by a RSF1010 mob-locus operably linked to a RSF1010 replicon.

2. The composite plasmid of claim 1 wherein said first DNA segment comprises a segment coding for antibiotic resistance and a restriction site unique to said first and second segments, said restriction site lying outside said segment coding for antibiotic resistance.

3. A composite plasmid according to claim 1 wherein the first DNA segment is derived from pACYC177, pACYC184 or pBR325.

4. A composite plasmid according to claim 3 selected from the group consisting of pSUP104, pSUP106, pSUP204, and pSUP304.

5. A composite plasmid according to claim 1 comprising a cosmid cloning site.

6. A composite plasmid according to claim 5 selected for stable replication in a RecA+ host cell when bearing an insert of about 30 to 40 kb in length.

7. The composite DNA plasmid of claim 1 wherein said composite DNA plasmid is stable in a RecA+ host when bearing an insert of about 30 to 40 kb in length.

8. A composite plasmid according to claim 7 wherein said first DNA segment comprises a segment coding for antibiotic resistance and a restriction site unique to said first and second segment, said restriction site lying outside said segment coding for antibiotic resistance.

9. A plasmid according to claim 7 wherein the first DNA segment is derived from pACYC177, pACYC184, or pBR325.

10. A plasmid according to claim 9 selected from the group consisting of pSUP104, pSUP106, pSUP204, and pSUP304.

11. A gram-negative bacterial cell containing and replicating therein the composite DNA plasmid of claim 1.

12. The bacterial cell of claim 11 wherein the first DNA segment of said composite DNA plasmid comprises a segment coding for antibiotic resistance and a restriction site unique to said first and second segments, said restriction site lying outside said segment coding for antibiotic resistance.

13. A bacterial cell according to claim 11 wherein the first DNA segment of the composite plasmid is derived from pACYC177, pACYC184 or pBR325.

14. A bacterial cell according to claim 11 wherein said composite plasmid is selected from the group consisting pSUP104, pSUP106, pSUP204, and pSUP304.

15. A bacterial cell according to claim 11 wherein said composite plasmid comprises a cosmid cloning site.

16. A bacterial cell according to claim 15 wherein the composite plasmid is selected for stable replication in in a RecA+ host cell when bearing an insert of about 30 to 40 kb in length.

17. A gram-negative bacterial cell containing and replicating therein the composite DNA plasmid of claim 7.

18. A bacterial cell according to claim 17 wherein the first DNA segment of said composite plasmid comprises a segment coding for antibiotic resistance and a restriction site unique to the first and second segments, said restriction site lying outside the segment coding for antibiotic resistance.

19. A bacterial cell according to claim 17 wherein the first DNA segment of said composite plasmid is derived from pACYC177, pACYC184 or pBR325.

20. A bacterial cell according to claim 19 wherein said composite plasmid is selected from the group consisting of pSUP104, pSUP106, pSUP204 and pSUP304.

21. A method for introducing the insert of claim 7 into a gram-negative bacterial cell and replicating the insert within said cell, comprising the steps of:
(a) inserting said insert into said composite DNA plasmid thereby forming an insert-bearing composite plasmid;
(b) transforming a mobilizing strain of *E. coli* with said insert-bearing composite plasmid;
(c) transferring said insert-bearing composite plasmid from said mobilizing strain to a gram-negative bacterial cell by conjugation; and
(d) selecting for a gram-negative transconjugant containing and replicating said insert-bearing composite plasmid.

22. The method of claim 21 wherein the mobilizing strain of *E. coli* contains chromosomally integrated DNA comprising DNA coding for tra functions derived from plasmid RP4.

23. The method of claim 21 wherein the mobilizing strain of *E. coli* is selected from the group consisting of S68-8, SM10 and S17-1.

24. The method of claim 21 wherein the first DNA segment of said composite plasmid comprises a segment coding for antibiotic resistance and a restriction site unique to said first and second segments, said restriction site lying outside the segment coding for antibiotic resistance.

25. The method of claim 21 wherein the first DNA segment of said composite plasmid is derived from pACYC177, pACYC184 or pBR325.

26. The method of claim 21 wherein the composite plasmid is selected from the group consisting of pSUP104, pSUP204, and pSUP304.

27. An isolated DNA molecule of RSF1010 having a maximum length of 6 kb, characterized by a RSF1010 mob-locus operably linked to a RSF1010 replicon, the functions of said mob-locus and said replicon being conferred upon a plasmid into which said DNA molecule is inserted.

* * * * *